(12) United States Patent
Mattke et al.

(10) Patent No.: US 9,321,720 B2
(45) Date of Patent: Apr. 26, 2016

(54) PROCESS FOR PREPARING ISOCYANATES

(75) Inventors: Torsten Mattke, Freinsheim (DE); Gerhard Olbert, Dossenheim (DE)

(73) Assignee: BASF SE, Ludwigshafen (DE)

( * ) Notice: Subject to any disclaimer, the term of this patent is extended or adjusted under 35 U.S.C. 154(b) by 156 days.

(21) Appl. No.: 13/273,734

(22) Filed: Oct. 14, 2011

(65) Prior Publication Data

US 2012/0095255 A1    Apr. 19, 2012

Related U.S. Application Data

(60) Provisional application No. 61/393,006, filed on Oct. 14, 2010.

(51) Int. Cl.
*C07C 263/10*    (2006.01)

(52) U.S. Cl.
CPC .................................... *C07C 263/10* (2013.01)

(58) Field of Classification Search
CPC combination set(s) only.
See application file for complete search history.

(56) References Cited

U.S. PATENT DOCUMENTS

| | | | |
|---|---|---|---|
| 8,558,026 B2 | 10/2013 | Olbert et al. | |
| 2003/0114705 A1 | 6/2003 | Friedrich et al. | |
| 2003/0216597 A1* | 11/2003 | Jenne et al. | 560/347 |
| 2004/0167354 A1 | 8/2004 | Biskup et al. | |
| 2005/0113601 A1* | 5/2005 | Herold et al. | 560/347 |
| 2006/0252960 A1 | 11/2006 | Sohn et al. | |
| 2007/0299279 A1 | 12/2007 | Pohl et al. | |
| 2009/0221846 A1* | 9/2009 | Wolfert et al. | 560/347 |
| 2009/0275775 A1* | 11/2009 | Kloetzer et al. | 560/344 |
| 2010/0041914 A1 | 2/2010 | Woelfert et al. | |
| 2010/0210870 A1* | 8/2010 | Olbert et al. | 560/347 |
| 2010/0305356 A1 | 12/2010 | Daiss et al. | |
| 2010/0317889 A1* | 12/2010 | Boehling et al. | 560/347 |
| 2011/0213177 A1 | 9/2011 | Mattke et al. | |
| 2011/0213178 A1 | 9/2011 | Mattke et al. | |
| 2011/0257428 A1 | 10/2011 | Knoesche et al. | |
| 2012/0016154 A1 | 1/2012 | Mattke et al. | |
| 2012/0197038 A1 | 8/2012 | Bohling et al. | |

FOREIGN PATENT DOCUMENTS

| | | | |
|---|---|---|---|
| CN | 101528678 A | | 9/2009 |
| CN | 101796022 A | | 8/2010 |
| DE | 102005042392 | * | 3/2007 |
| EP | 1 319 655 A2 | | 6/2003 |
| EP | 1 362 847 | | 11/2003 |
| EP | 1 449 826 | | 8/2004 |
| EP | 1 526 129 | | 4/2005 |

(Continued)

OTHER PUBLICATIONS

International Search Report, PCT/EP2011/067701, Oct. 11, 2011 Mailed Feb. 13, 2012.

(Continued)

*Primary Examiner* — Karl J Puttlitz
(74) *Attorney, Agent, or Firm* — Drinker Biddle & Reath LLP

(57) ABSTRACT

Process for preparing isocyanates by reacting the corresponding amines with phosgene comprising (a) providing at least one amine-comprising feed stream and at least one phosgene-comprising feed stream, (b) mixing the feed streams to form at least one reaction mixture in a mixing zone, (c) reacting the at least one reaction mixture in a reaction zone and (d) working-up the product mixture obtained from (c).

25 Claims, 1 Drawing Sheet

(56) References Cited

FOREIGN PATENT DOCUMENTS

| | | |
|---|---|---|
| JP | 2006-510692 A | 3/2006 |
| JP | 2008-007506 A | 1/2008 |
| JP | 2009-292197 A | 12/2009 |
| JP | 2009-292200 A | 12/2009 |
| JP | 2010-508373 A | 3/2010 |
| JP | 2011-132159 A | 7/2011 |
| JP | 2011-132160 A | 7/2011 |
| WO | WO-2007/028715 A1 | 3/2007 |
| WO | WO-2009/027232 A1 | 3/2009 |
| WO | WO 2009/027234 | 3/2009 |
| WO | WO-2010/010135 A1 | 1/2010 |
| WO | WO 2010/015667 | 2/2010 |
| WO | WO-2010/015667 A1 | 2/2010 |
| WO | WO 2010/043532 | 4/2010 |
| WO | WO 2010/052230 | 5/2010 |
| WO | WO 2010/063665 | 6/2010 |
| WO | WO 2010/100221 | 9/2010 |
| WO | WO 2010/106131 | 9/2010 |
| WO | WO 2010/115908 | 10/2010 |
| WO | WO 2011/018443 | 2/2011 |
| WO | WO 2011/036062 | 3/2011 |
| WO | WO 2011/067369 | 6/2011 |
| WO | PCT/EP2011/052658 | 9/2011 |
| WO | WO 2011/113737 | 9/2011 |
| WO | WO 2012/049158 | 4/2012 |

OTHER PUBLICATIONS

U.S. Appl. No. 61/308,318, filed Feb. 26, 2010, Mattke et al.
English Translation of the text of the first office action in China application No. 201180059870.0.
Japanese Office Action mailed Jul. 8, 2014 for Japanese Application No. 2013-533182.

* cited by examiner

PROCESS FOR PREPARING ISOCYANATES

CROSS-REFERENCE TO RELATED APPLICATIONS

This patent application claims the benefit of pending U.S. provisional patent application Ser. No. 61/393,006 filed Oct. 14, 2010 incorporated in its entirety herein by reference.

The invention relates to a process for preparing isocyanates by reacting the corresponding amines with phosgene, in which phosgene and amine are firstly mixed in a mixing zone and reacted to form isocyanate in a reaction zone. Here, the mixing zone and/or the reaction zone are made up of at least two independently regulable trains which each comprise at least one mixing unit and/or at least one reaction unit and are connected in parallel.

BACKGROUND OF THE INVENTION

The preparation of isocyanates by phosphenation of the corresponding amines can in principle be carried out by means of a liquid-phase phosgenation or a gas-phase phosgenation. Unlike the gas-phase phosgenation, the reaction in the liquid-phase phosgenation is carried out at low temperatures, and vaporization of the starting materials is not necessary.

In liquid-phase phosgenation, an amine-comprising feed stream in liquid form is fed in. This is mixed with a phosgene-comprising feed stream. The phosgene can here be dissolved in an inert solvent. The phosgene-comprising feed stream is subsequently injected into a mixing device in which it mixes with the amine-comprising feed stream. The amine and the phosgene react with liberation of HCl to form the corresponding isocyanate.

Rapid mixing of the amine with the phosgene is necessary since, at an insufficient phosgene concentration, the isocyanate formed reacts with the excess amine to form urea or other troublesome, high-viscosity and solid by-products. For this reason, rapid mixing and a short residence time in the reaction chamber are necessary.

A process for the liquid-phase phosgenation of amines for preparing isocyanates is described, for example, in WO 2010/015667 A1.

In gas-phase phosgenation, an amine-comprising feed stream and a phosgene-comprising feed stream, each in the gaseous state, are mixed. The amine and the phosgene react with liberation of HCl to form the corresponding isocyanate. The amine-comprising feed stream is generally present in liquid form and has to be vaporized and optionally superheated before mixing with the phosgene-comprising stream.

Owing to the low vapor pressure in particular of the diamines, the vaporization is carried out at elevated temperature. However, this can cause decomposition reactions of the amines or diamines, for example deaminations, demethylations and dimerizations, which have an adverse effect on the selectivity of the overall process.

In addition, reactions quickly commence on contacting of the two feed streams as a result of the high, temperatures. Apart from phosgenation of the amine to form isocyanate, it is possible for undesirable secondary and subsequent reactions to take place. Thus, for example, isocyanate which has already been formed can react with as yet unreacted amine to form a urea. Furthermore, carbodiimides and cyanurates can also be formed. This firstly affects the selectivity of the process, and, secondly, solid by-products which have been formed can lead to blockages and thus have an adverse effect on the running time of the plant. Efforts are therefore generally made to mix the feed streams as quickly as possible in order to avoid, as far as possible, mixing ratios which accelerate the formation of secondary components.

A process for preparing (poly)isocyanates in the gas phase with optimized mixing of the reactants is described, for example, in EP 1 319 655 A2.

Thus, mixing of the starting materials and the residence time of the reaction mixture in the corresponding reaction spaces are critical parameters both in gas-phase phosgenation and in liquid-phase phosgenation. The plants for preparing isocyanates by phosgenation of amines therefore have to be matched to the specific requirements in respect of rapid mixing of the feed streams and a narrow residence time window. Plants for the phosgenation of amines are designed essentially for the maximum streams of materials or for the respective nominal load. This means both mixing devices such as nozzles and also the reaction spaces, for example residence reactors, operate at the nominal load in the optimal region with optimized yield, purity of the products, etc. However, if the plant is not operating at full load, i.e. it is operated at only part of the nominal load, the residence times, for example; alter and the plant is no longer operating in the optimal region. This is the case, for example, during start-up and running-down, part loading of the plant or malfunctions in the plant. In these cases of reduced load, both the mixing devices and the residence reactors do not operate in the optimal region. The consequences are decreases in yield, fouling problems and/or reductions in quality.

It was therefore an object of the present invention to provide a process for preparing isocyanates by reading the corresponding amines with phosgene, which process can also be carried out at various load states without the above-described problems; in particular, mixing and/or the reaction should occur in the respective optimized residence time window even when the plant is operated at part load.

DETAILED DESCRIPTION OF THE INVENTION

Figure 1A:
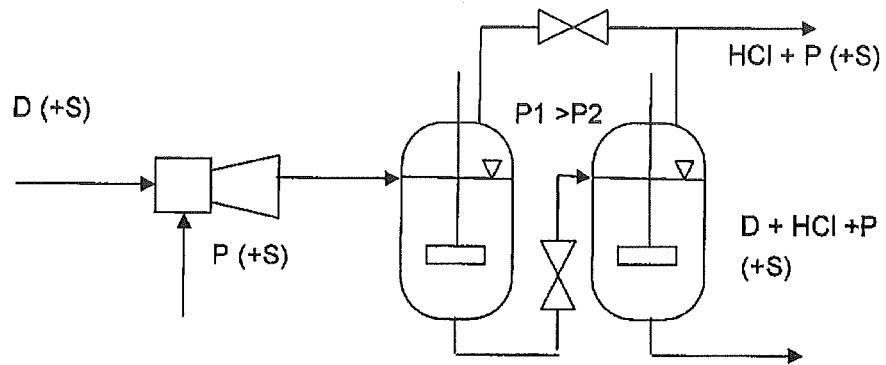
FIGS. 1a to 1c show three possible ways of carrying out the phosgenation in order to illustrate the process of the invention.

This object is achieved according to the invention by the following process for preparing isocyanates by reacting the corresponding amines with phosgene, which comprises the steps
(a) provision of at least one amine-comprising feed stream and at least one phosgene-comprising feed stream,
(b) mixing of the feed streams to form at least one reaction mixture in a mixing zone,
(c) reaction of the at least one reaction mixture in a reaction zone and
(d) work-up of the product mixture obtained from (c), wherein
(i) the mixing zone is made up of at least two independently regulable trains which each comprise at least one mixing unit and are connected in parallel or
(ii) the reaction zone is made up of at least two independently regulable trains which each comprise at least one reaction unit and are connected in parallel or
(iii) the mixing zone and the reaction zone are made up of at least two independently regulable trains which each comprise at least one mixing unit and at least one reaction unit and are connected in parallel.

For the purposes of the invention, "independently regulable" means that the individual, parallel trains can be shut off separately from one another and can each be operated independently of one another.

For the purposes of the invention, a "unit" (mixing unit, reaction unit or quenching unit) is in each case an apparatus in which the respective process step (mixing, reaction or quenching) can be carried out. As reaction unit, it is possible to use, for example, a tube reactor; as mixing unit it is possible to use a dynamic mixer having a rotor/stator system; and as quenching unit, it is possible to use an apparatus suitable for quenching.

Depending on the number N of the parallel trains, mixing unit(s) and reaction unit(s) are designed for a capacity of 1/N of the total capacity. In part load operation, only the required number of trains is started up, with these trains each running in the optimal region. The individual trains can each have the same capacity, i.e. be designed for the same nominal load, but the individual trains can also have different capacities or be designed for different nominal loads. According to the invention, preference is given to the mixing zone and the reaction zone each being made up of two trains which each have the same capacity, three trains which each have the same capacity or four trains which each have the same capacity. Here, a train comprises one or more units of the same kind, i.e. mixing units, reaction units, quenching units, which are connected in series or in parallel.

The process of the invention enables different amounts of desired product to be produced in one plant, with the optimal operating parameters for the individual trains always being able to be adhered to so that good and rapid mixing of the feed streams occurs in each case and/or the residence times of the feed streams or the product mixture are maintained at the values advantageous for the individual trains. This leads to smaller amounts of undesirable by-product. However, the advantages of a joint work-up of the product streams in one train can be utilized at the same time, for example by saving of additional tubes, distillation apparatuses, scrubbers, etc. Fewer fouling problems also occur. Furthermore, the process of the invention allows a subsequent increase in capacity in a comparatively simple manner since one or more new trains comprising one or more mixing units, reaction units and/or quenching units or further units for the work-up can be constructed while the existing trains can continue to be operated essentially without interruption.

If only the mixing zone is made up of at least two independently regulable trains connected in parallel (variant (i)), the reaction occurs in a joint reaction zone made up of at least one reaction unit. Here, the reaction mixtures coming from the at least two trains which each comprise at least one mixing unit are combined before entering the reaction zone, but it is also possible to feed the at least two reaction mixtures separately to the reaction zone and combine them in the reaction zone. Here, there are in each case as many reaction mixtures as trains which are taken into operation depending on the load level. An embodiment of variant (i) of the process of the invention is shown schematically in FIG. 1b.

If the reaction zone but not the mixing zone is made up of at least two trains connected in parallel (variant (ii)), the reaction mixture obtained in step (b) is, depending on the load level, divided over one or more of the at least two parallel trains which each comprise at least one reaction unit and make up the reaction zone.

According to the invention, preference is given to both the mixing zone and the reaction zone being made up of at least two independently regulable trains connected in parallel, with each train comprising at least one mixing unit and at least one reaction unit (variant (iii)). An embodiment of variant (iii) of the process of the invention is shown schematically in FIG. 1c.

To prepare the isocyanate, the at least one phosgene-comprising feed stream and the at least one amine-comprising feed stream are firstly fed to the mixing zone in which the mixing of amine-comprising feed stream and phosgene-comprising feed stream occurs to form a reaction mixture (step (b)). Here, care has to be taken to ensure sufficiently rapid mixing of the reactants. Methods of achieving short mixing times are known in principle. In the mixing units, it is possible to use mixing apparatuses having dynamic or static mixers. According to the invention, preference is given to using one or more static mixing devices in the mixing units. Suitable static mixing devices are, for example, nozzles, flat jet nozzles or Venturi nozzles and also Laval nozzles known from combustion technology. A particularly advantageous embodiment of a static mixing device is described in WO2010/015667 A1. As dynamic mixers, it is possible to use, for example, rotor/stator systems arranged in the mixing units. Preference is given, according to the invention, to using static mixing devices, in particular nozzles.

After mixing of the feed streams to form at least one reaction mixture, the reaction mixture is reacted in a reaction zone comprising at least one reaction unit (step (c)). Reactors which can be used as reaction units for phosgenation of an amine to produce isocyanates are known to those skilled in the art. A reaction zone preferably comprises at least one residence reactor. Preference is given to using reaction columns, tube reactors and/or cascades of stirred vessels as residence reactors.

In the reaction zone, the amine is reacted with the phosgene to form the corresponding isocyanate and hydrogen chloride. The phosgene is usually added in excess, so that the reaction mixture formed in the reaction zone comprises the isocyanate formed and the hydrogen chloride and also phosgene.

After step (c), the product mixture obtained in step (c) is worked up in step (d).

In a preferred embodiment of the invention, the work-up in step (d) of the process of the invention is carried out in a common train. This means that the product mixtures coming from the mixing zones and/or reaction zones made up of at least two independently regulable trains connected in parallel are optionally combined and worked up together in one train. Isolation of the desired isocyanates and removal of any solvents, inert gases, starting materials and quenching media comprised in the product mixture, any optional scrubbing of the product mixture and condensations are carried out jointly.

If one parallel train comprising one or more mixing units, reaction units and/or quenching units and/or further units for the work-up is shut down, the train in question or the one or more units in question are usually flushed after shutdown in order to recover any residual starting materials, residual products, etc., present and/or to clean the train or units which have been shut down. Conversely, when a parallel train comprising one or more mixing units, reaction units and/or quenching units and/or further units for the work-up of the at least one product mixture obtained from step (c) is started up, these units can be flushed and/or filled with the appropriate starting materials/reaction mixtures, etc., before being started up. The at least two independently regulable trains connected in parallel which are present according to the process of the invention therefore generally also comprise the appropriate apparatuses which are customarily used by a person skilled in the art for flushing/introduction, etc.

The process of the invention is suitable both for gas-phase phosgenation and for liquid-phase phosgenation.

In an embodiment of the invention, the reaction of amine and phosgene in the reaction zone occurs in the gas phase. For this purpose, the pressure in the reaction zone is usually in the range from 0.3 to 3 bar absolute, preferably in the range from 0.8 to 3.0 bar absolute. The temperature is usually in the range from 250 to 550° C., preferably in the range from 300 to 500° C.

To be able to carry out the reaction in the gas phase, the amine and the phosgene are preferably introduced in gaseous form. For this purpose, the amine preferably has a temperature in the range from 200 to 400° C. The pressure in the mixing zone is preferably in the range from 0.05 to 3 bar absolute and the temperature in the mixing zone is in the range from 200 to 400° C. The temperature in the mixing zone is determined by the temperature of the phosgene and amine flowing into the mixing zone. The temperature of the phosgene introduced is preferably in the range from 250 to 450° C. For this purpose, the phosgene is usually heated in a manner known to those skilled in the art before introduction.

Heating of the phosgene and the amine and vaporization of the amine are carried out using, for example, electric heating or direct or indirect heating by combustion of a fuel. Fuels used are usually fuel gases, for example natural gas. However, heating by means of, for example, steam is also possible when the boiling point is reduced by decreasing the pressure of the amine. The pressure of the steam is selected as a function of the boiling point of amine. A suitable steam pressure is, for example, in the range from 40 to 100 bar. This corresponds to a temperature of the steam in the range from 250 to 311° C. However, it is also possible to use steam having a temperature of greater than 311° C. for vaporizing the amine.

It is generally necessary to heat the amine in a number of stages to the reaction temperature. In general, the amine is for this purpose firstly preheated, then vaporized and subsequently superheated. In general, the vaporization requires the longest residence times and thus leads to decomposition of the amine. To minimize this, vaporization at relatively low temperatures, as results, for example, from the lower pressure, is advantageous. To superheat the vaporized amine to the reaction temperature after vaporization, heating by means of steam is generally not sufficient. Superheating is therefore usually carried out using electric heating or direct or indirect heating by combustion of a fuel.

In contrast to the vaporization of the amine, the vaporization of the phosgene is generally carried out at significantly lower temperatures. For this reason, steam can generally be used for vaporizing the phosgene. However, the superheating of the phosgene which is required to heat this to the reaction temperature is generally also possible only by means of electric heating or direct or indirect heating by combustion of a fuel.

Preferably, the at least one amine-comprising feed stream and the at least one phosgene-comprising feed stream are in each case converted into the gaseous phase in at least one vaporization zone and optionally superheated further in at least one superheating zone. The vaporization zone and/or the superheating zone can be made up of at least two independently regulable trains which each comprise at least one vaporization unit and/or at least one superheating unit and are connected in parallel. Preference is given to both the vaporization zone and the superheating zone each being made up of one train.

The at least one amine-comprising feed stream can be vaporized in a vaporization zone made up of at least two independently regulable trains which each comprise at least one vaporization unit and are connected in parallel. The at least one amine-comprising feed stream can also be superheated in at least one superheating zone made up of at least two independently regulable trains which each comprise at least one superheating unit and are connected in parallel. Preference is given to the at least one amine-comprising feed stream being both converted into the gaseous phase in at least one vaporization zone and superheated in at least one superheating zone, each of which are made up of at least two independently regulable trains which each comprise at least one vaporization unit and at least one superheating unit and are connected in parallel.

The same applies to the at least one phosphene-comprising feed stream. Preference is given to both the at least one amine-comprising feed stream and the at least one phosgene-comprising feed stream being in each case converted into the gaseous phase in at least one vaporization zone and superheated in at least one superheating zone. Both the vaporization zone and the heating zone can in each case be made up of at least two independently regulable trains which each comprise at least one vaporization unit and at least one superheating unit and are connected in parallel. Preference is given to both the vaporization zone and the superheating zone each being made up of one train.

The reaction in the gas phase can be carried out in the presence of at least one inert medium. The inert medium can be added to the phosgene-comprising feed stream and/or to the amine-comprising feed stream.

Inert media which can be added are ones which are present in gaseous form in the reaction space and do not react with the compounds occurring in the course of the reaction. As inert medium, it is possible to use, for example, nitrogen, noble gases such as helium or argon, aromatics such as chlorobenzene, o-dichlorobenzene, trichlorobenzene, toluene, xylene, chloronaphthalene, decahydronaphthalene, carbon dioxide or carbon monoxide. However, preference is given to using nitrogen and/or chlorobenzene as inert medium.

In general, the inert medium is used in such an amount that the ratio of the gas volumes of inert medium to amine and to phosgene is from <0.0001 to 30, preferably from <0.01 to 15 and particularly preferably from <0.1 to 5.

To avoid formation of by-products, phosgene is preferably introduced in excess. In order to introduce only the proportion of amines necessary for the reaction, it is possible to mix the amine with an inert gas. The amount of amine fed in at a prescribed geometry of the inlet openings for the amine and the phosgene can be adjusted via the proportion of inert gas in the amine.

It is desirable in the gas-phase phosgenation that the compounds occurring during the course of the reaction, i.e. starting materials (amine and phosgene), intermediates (in particular the monocarbamoyl and dicarbamoyl chlorides formed as intermediates), end products (diisocyanate) and also any inert compounds fed in, remain in the gas phase under the reaction conditions. Should these or other components separate out from the gas phase, for example on the reactor wall or other components of the apparatus, the heat transfer or the flow through the components concerned can be undesirably altered by these deposits. This applies particularly in the event of deposition of the amine hydrochlorides which are formed from free amino groups and hydrogen chloride, since the resulting amine hydrochlorides precipitate easily and are difficult to vaporize again.

To reduce or avoid the formation of undesirable by-products and also supress decomposition of the isocyanate formed, the reaction gas is preferably cooled in a quench immediately after the reaction. For this purpose, a preferably liquid quenching medium is introduced. Vaporization of the quenching medium takes up heat and leads to rapid cooling of the reaction gases.

In a preferred embodiment of the process, the at least one product mixture obtained from step (c) in the gas-phase phosgenation is cooled in at least one quenching zone, Quenching is carried out in a quenching zone made up of one or at least two independently regulable trains which each comprise at least one quenching unit and are connected in parallel. When the phosgenation is carried out in the gas phase according to the invention, the mixing zone (step (b)) and/or the reaction zone (step (c)) and/or quenching (as part of the work-up in step (d) of the at least one reaction mixture obtained from step (c)) can thus be made up of at least two independently regulable trains connected in parallel, with the trains comprising, depending on the embodiment, at least one mixing unit and/or at least one reaction unit and also at least one quenching unit.

The process of the invention is particularly preferably carried out with the mixing zone, the reaction zone and the quenching zone being made up of at least two independently regulable trains which are connected in parallel, with each of these parallel trains comprising at least one mixing unit, at least one reaction unit and at least one quenching unit. For example, the process can be carried out using two independently regulable trains connected in parallel, with each of the two trains comprising at least one mixing unit, at least one reaction unit and at least one quenching unit, so that the mixing zone, the reaction zone and the quenching zone are each made up of two independently regulable trains connected in parallel. A train can comprise one or more units of the same kind, i.e. mixing units, reaction units, quenching units, which are connected in series or in parallel.

Rapid cooling is achieved, in particular, by the quenching medium being introduced in finely atomized form. As a result, the quenching medium has a large surface area and can quickly take up heat and thus cool the reaction gas.

Particularly when a quenching medium which under the conditions in the quenching space has a boiling point below the condensation temperature of the reaction gas is used, the pressure in the feed lines is higher than the pressure in the quenching space in order to avoid vaporization of the quenching medium before introduction into the quenching space.

The pressure at which the quenching medium is introduced is preferably in the range from 1 to 20 bar, more preferably in the range from 1 to 10 bar and in particular in the range from 1 to 8 bar.

The quenching medium used for cooling preferably comprises a solvent selected from the group consisting of monochlorobenzene, dichlorobenzene, trichlorobenzene, hexane, benzene, 1,3,5-trimethylbenzene, nitrobenzene, anisole, chlorotoluene, o-dichlorobenzene, diethyl isophthalate, tetrahydrofuran, dimethylformamide, xylene, chloronaphthalene, decahydronaphthalene and toluene.

The quenching medium preferably comprises part of the product stream cooled in the quench; particular preference is given to using part of the product stream which has already been cooled in the quench as quenching medium. In this case, the quenching medium usually does not comprise any solvent but only the part of the product stream condensed out during quenching.

To avoid formation of deposits in pipes, regulating devices and other parts of the apparatus, in particular in the atomizer nozzles of the quench, any solid particles comprised in the quenching medium are removed before introduction into the quench.

When an isocyanate is present in the quenching medium, particular preference is given to the isocyanate formed in the reaction firstly being cooled in the quench and optionally in subsequent cooling stages and, after cooling, a substream being used as quenching medium.

The quenching medium is preferably introduced in liquid form to achieve rapid cooling of the reaction gas in the quench. The temperature of the quenching medium is preferably in the range from 0 to 250° C., in particular in the range from 20 to 220° C. Introduction of the quenching medium into the hot reaction gas results in the quenching medium being heated and/or vaporized. The heat necessary for heating and vaporization of the quenching medium is taken from the reaction gas and the reaction gas is cooled in this way. The temperature to which the reaction gas is cooled can be set, for example, via the amount and the temperature of the quenching medium introduced.

To adjust, if necessary, the temperature of the quenching medium when introduced into the quench, the quenching medium is preferably passed through a heat exchanger.

Depending on the temperature of the quenching medium on entry into the heat exchanger, the quenching medium can be heated or cooled in the heat exchanger. Cooling is necessary when, for example, part of the product stream which is used as quenching medium is taken off immediately after the quench. Heating can be required when, for example, part of the product stream which is used as quenching medium is taken off at the end of the treatment section and has a temperature which is lower than the desired temperature at which the quenching medium is to be introduced into the quench. However, it will generally be necessary to cool the quenching medium before introduction into the quench.

When the quenching medium comprises solvent, the solvent/solvents is/are preferably added to the quenching medium before introduction into the quench. Solvent losses in the quenching medium can be compensated in this way. Suitable solvents which can be comprised in the quenching medium are, for example, optionally halogen-substituted hydrocarbons. The solvent comprised in the quenching medium is preferably selected from the group consisting of monochlorobenzene, dichlorobenzene, trichlorobenzene, hexane, benzene, 1,3,5-trimethylbenzene, nitrobenzene, anisole, chlorotoluene, o-dichlorobenzene, diethyl isophthalate, dimethyl isophthalate, tetrahydroforan, dimethylformamide, xylene, chloronaphthalene, decahydronaphthalene and toluene.

In a preferred embodiment the quench is followed, to effect further treatment, by further stages for cooling the reaction gas. In each of the individual cooling stages, further cooling of the product stream occurs until the desired temperature at which the product stream is fed to, for example, a subsequent work-up has been reached. Preference is given to the entire stream leaving the quench, which comprises both the quenching medium and the reaction mixture, being used as product stream in the quench.

The further cooling stages which can follow the quench can, for example, be further quenches or condensors or in any other cooling stages known to those skilled in the art. Preference is given to at least one of the stages for cooling the product stream which follow the quench being a condensor. Suitable condensors are any condensors having a construction known to those skilled in the art. A heat exchanger through which a cooling medium flows is usually used as condensor. As coolant, it is possible, for example, to use water. In this case, the gas condenses at least partly on the walls of the condensor. The liquid formed in this way runs down and is collected and taken Off from the condensor.

The condensation of the product stream is generally followed by a work-up. It is thus possible, for example, to scrub the condensed mixture in a solvent. As solvent, it is possible to use, for example, the same materials which can also be used as quenching medium.

It is also possible, for example, to scrub the reaction gas leaving the quench and any cooling stages following this by means of a solvent, preferably at temperatures of greater than 130° C. Suitable solvents are, for example, the same materials which can also be used as quenching medium.

As an alternative to cooling the product stream, it is also possible to feed the product stream leaving the quench to a separation stage. However, such a separation stage can, as an alternative, also follow, for example, the condensor. However, the separation stage preferably directly follows the quench. Suitable separation stages are, for example, distillation columns or scrubbers.

When the separation stage is a scrubber, the product stream leaving the quench is preferably scrubbed by means of a solvent. Here, the isocyanate is selectively transferred into the scrubbing solution. The remaining gas and the scrubbing solution obtained are then preferably separated by means of rectification into Isocyanate, solvent, phosgene and hydrogen chloride. A suitable scrubber is, in particular, a scrubbing tower in which the isocyanate formed is separated from the gaseous product stream by condensation in an inert solvent, while excess phosgene, hydrogen chloride and optionally the inert medium pass through the scrubbing tower in gaseous form. The temperature of the inert solvent is preferably kept above the dissolution temperature of the carbamoyl chloride corresponding to the amine in the scrubbing medium selected. The temperature of the inert solvent is preferably kept above the melting point of the carbamoyl chloride corresponding to the amine.

Suitable scrubbers are any scrubbers known to those skilled in the art. Thus, for example, it is possible to use stirred vessels or other conventional apparatuses, for example columns or mixer-settler apparatuses.

The scrubbing and the work-up of the mixture of reaction gas and quenching medium leaving the quench is generally carried out as described, for example, in WO-A 2007/028715.

When the separation stage is a distillation column, also referred to as rectification column, the gaseous product stream is fed into the rectification column. The rectification column is preferably operated in such a way that the temperature at the top of the rectification column is lower than the boiling point of the product stream. As a result, individual constituents of the product stream are condensed out selectively in the distillation column and can be taken off from the column at the bottom, overhead and optionally via side offtakes.

When a condensor is used for working up the product stream, the quenching medium is preferably taken off from the condensor. In the case of a work-up by rectification, the solvent used as quenching medium is preferably separated off. In this case, the solvent still comprises proportions of isocyanates. The mixture of solvent and isocyanate which has been separated off in this way is then used as quenching medium.

When part of the product stream is used as quenching medium, it is possible, for example, to branch off this part from the product stream after cooling. As an alternative, the quenching medium can also be branched off from any stream after a work-up following the quench.

In a further embodiment of the invention, the reaction is carried out in the liquid phase. This embodiment will be described in detail below. According to the invention, the amine is preferably present as solution or as suspension in the at least one amine-comprising feed stream.

As feed streams for the process of the invention with liquid-phase phosgenation, use is usually made of, firstly, from 3% strength by weight to 100% strength by weight, preferably from 50% strength by weight to 100% strength by weight, phosgene solutions and, secondly, from 5% strength by weight to 95% strength by weight solutions or suspensions of amines or salts thereof in suitable solvents.

Suitable solutions for producing the phosgene solutions and amine solutions or suspensions are any solvents which are inert under the reaction conditions, for example monochlorobenzene, o-dichlorobenzene, trichlorobenzene, toluene, xylene, methylene chloride, perchloroethylene, trichlorofluoromethane, butyl acetate, hexane, heptane, octane, biphenyl, ethyl acetate, 1,2-diacetoxyethane, 2-butanone, acetonitrile and sulfane. Any mixtures of the solvents mentioned by way of example can of course also be used. It is advantageous to use the same solvent or solvent mixture for the amine component and the phosgene, although this is not absolutely necessary for the purposes of the invention.

In a preferred embodiment of the invention, the introduction of the starting materials is set and/or regulated so that the phosgene solutions and amine solutions or amine suspensions are introduced into the mixing chamber in such amounts that a molar ratio of phosgene to primary amino groups of from about 15:1 to 1:1, preferably from 10:1 to 2:1, prevails in the mixing chamber.

In a preferred embodiment, the solution of phosgene, i.e. the phosgene-comprising feed stream, is free of isocyanates. This means that isocyanates are present in an amount of less than or equal to 5% by weight, preferably less than 2% by weight, in particular less than 1% by weight, in the phosgene-comprising feed stream. Particular preference is given to no Isocyanates being comprised in the phosgene-comprising feed stream, i.e. these cannot be detected by conventional analytical methods. This can advantageously significantly reduce the formation of reaction by-products such as urea derivatives which have an adverse effect on the selectivity of the process and can lead to fouling of the plant through to blockages. The formation of urea derivatives is thus reduced by no isocyanates which can lead to formation of urea derivatives on contact with amines being introduced as starting materials into the process.

When carrying out the process with liquid-phase phosgenation, the temperature in the mixing zone is usually kept at a temperature above the decomposition temperature of the carbamoyl chloride corresponding to the amine used. In the case of most amities, the process of the invention is carried out at a temperature of from about 30° C. to 300° C., preferably from about 40° C. to 150° C., particularly preferably from about 50° C. to 120° C.

The phosgenation in the liquid phase according to the invention gives at least one product mixture which is usually fed directly to the work-up and is there partially separated into HCl, phosgene, solvents and also products and by-products formed.

In general, the amines known to those skilled in the art for the preparation of isocyanates can be used in the process of the invention. These are, for example, monoamines, diamines, triamines and higher-functional amines. Preference is given to using monoamines and diamines, particularly preferably diamines. Depending on the amines used, the corresponding monoisocyanates, diisocyanates, triisocyanates or higher-functional isocyanates are obtained. Preference is given to preparing monoisocyanates or diisocyanates by the process of the invention.

Amines and isocyanates can be aliphatic, cycloaliphatic or aromatic. The amines are preferably aliphatic or cycloaliphatic, particularly preferably aliphatic.

Cycloaliphatic isocyanates are those which comprise at least one cycloaliphatic ring system.

Aliphatic isocyanates are those which have exclusively isocyanate groups bound to straight or branched chains.

Aromatic isocyanates are those which have at least one isocyanate group bound to at least one aromatic ring system.

In the following, the term (cyclo)aliphatic isocyanates will be used for cycloaliphatic and/or aliphatic isocyanates.

Examples of aromatic monoisocyanates and diisocyanates are preferably those having from 6 to 20 carbon atoms, for example phenyl isocyanate, monomeric 2,4'- and/or 4,4'-methylenedi(phenyl isocyanate) (MDI) and higher oligomers thereof (polymethylenedi(phenyl isocyanate) (PDMI) and mixtures thereof, tolylene 2,4- and/or 2,6-diisocyanate (TDI) and naphthyl 1,5- or 1,8-diisocyanate (NDI).

Examples of (cyclo)aliphatic diisocyanates are aliphatic diisocyanates such as tetramethylene 1,4-diisocyanate, hexamethylene 1,6-diisocyanate (1,6-diisocyanatohexane), octamethylene 1,8-diisocyanate, decamethylene 1,10-diisocyanate, dodecamethylene 1,12-diisocyanate, tetradecamethylene 1,14-diisocyanate, 1,5-diisocyanatopentane, neopentane diisocyanate, 2-methyl-1,5-diisocyanatopentane, derivates of lysine diisocyanate, tetramethylxylylene diisocyanate (TMXDI), trimethylhexane diisocyanate or tetramethylhexane diisocyanate, and 3(or 4),8(or 9)-bis(isocyanatomethyl)tricyclo[5.2.1.0$^{2.6}$]decane isomer mixtures, and also cycloaliphatic diisocyanates such as 1,4-, 1,3- or 1,2-diisocyanatocyclohexane, 4,4'- or 2,4'-di(isocyanatocyclohexyl)methane, 1-isocyanato-3,3,5-trimethyl-5-(isocyanatomethyl)cyclohexane (isophorone diisocyanate), 1,3- or 1,4-bis(isocyanatomethyl)cyclohexane, 2,4- or 2,6-diisocyanato-1-methylcyclohexane.

Preferred (cyclo)aliphatic diisocyanates are 1,6-diisocyanatohexane, 1-isocyanato-3,3,5-trimethyl-5-(isocyanatomethyl)cyclohexane and 4,4'-di(isocyanatocyclohexyl)methane. Particular preference is given to 1,6-diisocyanatohexane, 1,5-diisocyanatopentane, 1-isocyanato-3,3,5-trimethyl-5-(isocyanatomethyl)cyclohexane and 4,4'-di(isocyanatocyclohexyl)methane.

Suitable amines which can be used in the process of the invention with gas-phase phosgenation for reaction to form the corresponding isocyanates are those in the case of which the amine, the corresponding intermediates and the corresponding isocyanates are present in gaseous form under the selected reaction conditions. Preference is given to amines which decompose to an extent of not more than 2 mol %, particularly preferably not more than 1 mol % and very particularly preferably not more than 0.5 mol %, under the reaction conditions during the time of the reaction. Particularly suitable amines here are amines, in particular diamines, based on aliphatic or cycloaliphatic hydrocarbons having from 2 to 18 carbon atoms. Examples are 1,6-diaminohexane, 1,5-diaminopentane, 1,3-bis(aminomethyl)cyclohexane, 1-amino-3,3,5-trimethyl-5-aminomethylcyclohexane (IPDA) and 4,4'-diaminodicyclohexylmethane. Preference is given to using 1,6-diaminohexane (HDA).

The process of the invention with gas-phase phosgenation can likewise be carried out using aromatic amines which can be converted without significant decomposition into the gas phase. Examples of preferred aromatic amines are toluenediamine (TDA), as 2,4 or 2,6 isomer or as a mixture thereof, for example as a from 80:20 to 65:35 (mol/mol) mixture, diaminobenzene, 2,6-xylidine, naphthyldiamine (NDA) and 2,4'- or 4,4'-methylenedi(phenylamine) (MDA) or isomer mixtures thereof. Among these, preference is given to the diamines, particularly preferably 2,4- and/or 2,6-TDA and also 2,4'- and/or 4,4'-MDA.

In the gas-phase phosgenation according to the process of the invention, the amine is particularly preferably selected from the group consisting of 1,6-diaminohexane, monomeric 2,4'-methylenedi(phenylamine), monomeric 4,4'-methylenedi(phenylamine), 2,4-toluenediamine, 2,6-toluenediamine, 1-amino-3,3,5-trimethyl-5-aminomethylcyclohexane and mixtures thereof.

Particularly suitable amines for the process of the invention with liquid-phase phosgenation are any primary monoamines and polyamines such as methylamine, ethylamine, butylamine, stearylamine, phenylamine, p-toluidine, 1,4-diaminobutane, 1,6-diaminohexane, 1,8-diaminooctane, 1,4-diaminobenzene, 2,4-diaminotoluene, 2,6-diaminotoluene, mixtures of the last two isomers mentioned, 2,2'-diaminodiphenylmethane, 2,4'-diaminodiphenylmethane, 4,4'-diaminodiphenylmethane, mixtures of the last three isomers mentioned, alkyl substituted diamines of the diphenylmethane series, for example 3, 4'-diamino-4-methyldiphenylmethane, polyamine mixtures of the diphenylmethane series as are obtained in a known manner by aniline-formaldehyde condensations, p-xylenediamine, perhydrogenated 2,4- and/or 2,6-diaminotoluene, 2,2'-, 2,4'- and/or 4,4'-diaminodicyclohexylmethane, 1-amino-3,3,5-trimethyl-5-aminomethylcyclohexane (isophoronediamine, IPDA for short), the ethyl ester of lysine, the aminoethyl ester of lysine, 2,4- and 2,6-toluenediamine and 1,6,11-triaminoundecane.

Figure 1B:
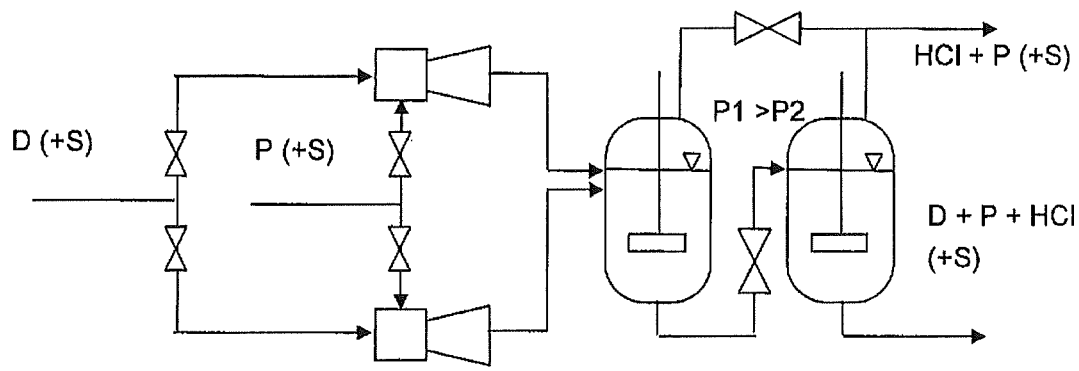
Figure 1C:
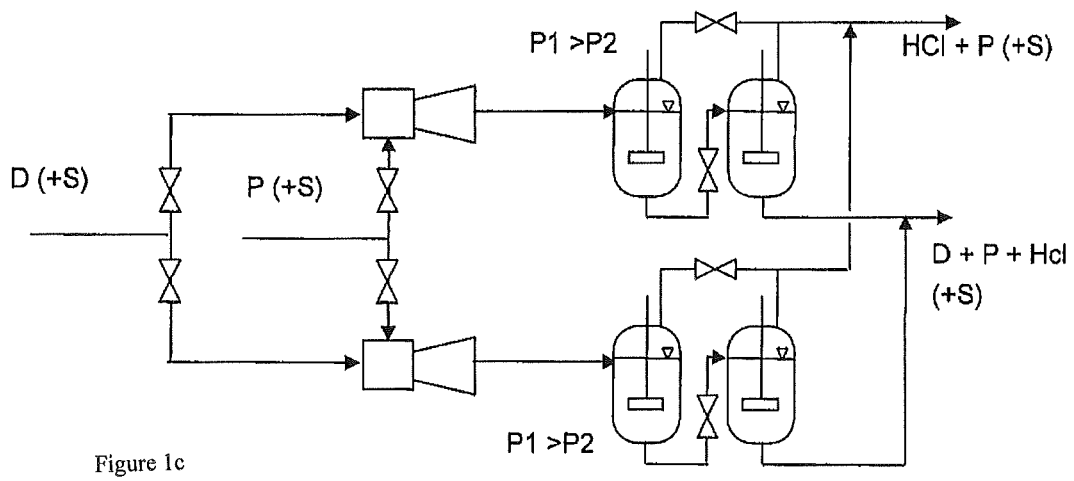

FIGS. 1a to 1c schematically show three possible ways of carrying out the phosgenation in order to illustrate the process of the invention. FIG. 1a shows the conventional phosgenation of amines to form isocyanates, in which mixing of the starting materials and reaction of the reaction mixture are each carried out in one train (not according to the invention). FIG. 1b shows an embodiment of variant (i) according to the invention, in which the mixing zone is made up of two independently regulable trains which each comprise a mixing unit and are connected in parallel. FIG. 1c shows an embodiment of variant (iii) according to the Invention, in which both the mixing zone and the reaction zone are made up of two independently regulable trains which each comprise a mixing unit and a reaction unit and are connected in parallel. "A" denotes amine, optionally mixed with solvent "(+S)", "P" denotes phosgene, optionally mixed with solvent "(+S)", "S" denotes solvent and "I" denotes isocyanate. P1>P2 means that the pressure in the first reaction unit is higher than that in the second reaction unit.

The invention will be illustrated below with the aid of examples calculated from thermodynamic and kinetic data.

COMPARATIVE EXAMPLE 1

In a plant for preparing tolylene diisocyanate (TDI) by phosgenation of TDA in the liquid phase, a 30% strength solution of toluenediamine (TDA) in monochlorobenzene is mixed with a phosgene stream in a mixing nozzle (mixing time: 11.7 ms). The molar ratio of phosgene to TDA is 10. The mixing temperature of the streams is about 60° C. An adiabatic tube reactor having a residence time of about 2 minutes is installed downstream of the mixing nozzle. The reaction of the amine to form isocyanate or the carbamoyl chloride as precursor occurs in this. As a result of the adiabatic temperature increase and liberation of HCl, a gas phase is formed. The two-phase reaction mixture is subsequently fed to a reaction column.

The yield in the reaction stage in respect of TDA is 93.4%.

COMPARATIVE EXAMPLE 2

The above-described plant is to produce only 50% of its nominal load. Accordingly, amine-comprising and phosgene-comprising feed streams are halved. As a result, the mixing time increases to 23.4 ms. At the same time, the residence time in the reactor doubles. The yield of TDI drops from 93.4% to 80.2%.

EXAMPLE 1 ACCORDING TO THE INVENTION

Two parallel nozzles are installed according to the invention in the above-described plant. Each of these is designed for 50% of the total nominal load of the plant, so that the mixing time mentioned in example 1 is realized. During operation of the plant at 50% of the nominal load, one of the nozzles is shut off. The second nozzle is accordingly operated at its design load, so that the mixing time remains 11.7 ms. Accordingly, 93.4% yield is achieved at the same specific energy costs and therefore without the disadvantages of comparative example 2.

The invention claimed is:

1. A process for preparing isocyanates, which comprises the steps of:
   (a) providing at least one amine-comprising feed stream and at least one phosgene-comprising feed stream,
   (b) mixing the feed streams to form at least one reaction mixture in a mixing zone,
   (c) reacting the at least one reaction mixture in a reaction zone to obtain a product mixture, and
   (d) working up the product mixture obtained from (c), wherein
   (i) the mixing zone is made up of at least two independently regulatable trains which each comprise at least one mixing unit and are connected in parallel; or
   (ii) the mixing zone and the reaction zone are made up of at least two independently regulatable trains which each comprise at least one mixing unit and at least one reaction unit and are connected in parallel.

2. The process according to claim 1, wherein the mixing unit(s) comprise static mixing devices.

3. The process according to claim 1, wherein the reaction unit(s) comprise at least one residence reactor.

4. The process according to claim 3, wherein the at least one residence reactor is a tube reactor and/or cascade of stirred vessels.

5. The process according to claim 1, wherein the working up in step (d) is carried out in a common train.

6. The process according to claim 1, wherein the reaction is carried out in the liquid phase.

7. The process according to claim 6, wherein the at least one amine-comprising feed stream comprises an amine present as solution or as suspension.

8. The process according to claim 6, wherein the at least one amine-comprising feed stream comprises an amine in a concentration of from 5 to 95% by weight, based on the at least one amine-comprising feed stream provided, and the molar ratio of the phosgene to the amine in the feed streams is in the range of from 15:1 to 1:1.

9. The process according to claim 6, wherein the amine is selected from the group consisting of methylamine, ethylamine, butylamine, stearylamine, phenylamine, p-toluidine, 1,4-diaminobutane, 1,6-diaminohexane, 1,8-diaminooctane, 1,4-diaminobenzene, 2,4- and/or 2,6-diaminotoluene, 2,2'-diaminodiphenylmethane, 2,4'-diaminodiphenylmethane, 4,4'-diaminodiphenylmethane, alkyl substituted diamines of the diphenylmethane series, polyamine mixtures of the diphenylmethane series as are obtained in a known manner by aniline-formaldehyde condensations, p-xylenediamine, perhydrogenated 2,4-diaminotoluene, perhydrogenated 2,6-diaminotoluene, 2,2'-diaminodicyclohexylmethane, 2,4'-diaminodicyclohexylmethane, 4,4'-diaminodicyclohexylmethane, 1-amino-3,3,5-trimethyl-5-aminomethylcyclohexane, the ethyl ester of lysine, the aminoethyl ester of lysine, 2,4-toluenediamine, 2,6-toluenediamine, 1,6,11-triaminoundecane and mixtures thereof.

10. The process according to claim 9, wherein the alkyl substituted diamine of the diphenylmethane series is 3,4'-diamino-4-methyldiphenylmethane.

11. The process according to claim 6, wherein monochlorobenzene, odichlorobenzene, trichlorobenzene, toluene, xylene, methylene chloride, perchloroethylene, trichlorofluoromethane, butyl acetate, hexane, heptane, octane, biphenyl, ethyl acetate, 1,2-diacetoxyethane, 2-butanone, acetonitrile, sulfane, or mixtures thereof are used as solvents for the starting materials.

12. The process according to claim 1, wherein the reaction is carried out in the gaseous phase.

13. The process according to claim 12, wherein the at least one product mixture obtained from step (c) is cooled in at least one quenching zone.

14. The process according to claim 13, wherein the mixing zone, the reaction zone, and the quenching zone comprise at least two independently regulatable trains connected in parallel, where each of these parallel trains comprises at least one mixing unit, at least one reaction unit, and at least one quenching unit.

15. The process according to claim 12, wherein the reaction is carried out in the presence of at least one inert medium.

16. The process according to claim 12, wherein the amine is selected from the group consisting of 1,6-diaminohexane, monomeric 2,4'-methylenedi(phenylamine), monomeric 4,4'-methylenedi(phenylamine), 2,4-toluenediamine, 2,6-toluenediamine, 1-amino-3,3,5-trimethyl-5-aminomethylcyclohexane, and mixtures thereof.

17. A process for preparing isocyanates, which comprises the steps of:
   (a) providing at least one amine-comprising feed stream and at least one phosgene-comprising feed stream;
   (b) mixing the feed streams in a mixing zone that includes at least two independently regulatable mixing trains connected in parallel to provide at least two reaction mixtures, wherein each of the at least two mixing trains includes at least one mixing unit;
   (c) reacting the at least two reaction mixtures in a reaction zone that includes at least two independently regulatable trains connected in parallel to provide at least two product mixtures, wherein each of the at least two reaction trains includes at least one reaction unit; and
   (d) combining the at least two product mixtures for work up.

18. The process according to claim 17, wherein the reaction is carried out in the liquid phase, and the at least one amine-comprising feed stream comprises an amine present as solution or as a suspension.

19. The process according to claim 18, wherein the amine is an alkyl substituted diamine of diphenylmethane.

20. A process for preparing isocyanates, which comprises the steps of:
   providing at least one amine-comprising feed stream and at least one phosgene-comprising feed stream;

mixing the feed streams in a mixing zone that includes at least two independently regulatable mixing trains connected in parallel to provide at least two reaction mixtures, wherein each of the at least two mixing trains includes at least one mixing unit;

reacting the at least two reaction mixtures in a reaction zone that includes at least one regulatable reaction train that includes at least one reaction unit to obtain a product mixture; and working up the product mixture.

21. The process according to claim 13, wherein the quenching zone includes a quenching medium maintained at a temperature in the range from 0 to 250°.

22. The process according to claim 12, wherein the pressure in the mixing zone is the range from 0.3 to 3 bar absolute.

23. The process according to claim 6, wherein isocyanates are present in an amount of less than or equal to 5% by weight in the phosgene-comprising feed stream.

24. The process according to claim 6, wherein the process of the invention is carried out at a temperature of from about 40° C. to 150° C.

25. The process according to claim 1, wherein the process is carried out in the gas phase or in the liquid phase and wherein the pressure in the mixing zone is in the range of 0.3 to 3 bar absolute if the process is carried out in the gas phase and wherein the isocyanates are present in an amount of less than or equal to 5% by weight in the phosgene-comprising feed stream if the process is carried out in the liquid phase.

\* \* \* \* \*